US00PP13885P39

(12) United States Plant Patent
Pieters

(10) Patent No.: US PP13,885 P3
(45) Date of Patent: Jun. 17, 2003

(54) CHRYSANTHEMUM PLANT NAMED 'GEDI ONE TER'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 09/873,962

(22) Filed: Jun. 4, 2001

(65) Prior Publication Data

US 2002/0184679 P1 Dec. 5, 2002

(51) Int. Cl.[7] ..... A02H 5/00

(52) U.S. Cl. ..... Plt./288

(58) Field of Search ..... Plt./288, 287

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar characterized by large decorative type inflorescences, consistent flowering response to short days, blooming consistently after 49 days of short day length, free branching habit, and a consistent natural season flowering habit during the last two weeks of August.

1 Drawing Sheet

LATIN NAME

*Dendranthema morifolium*

VARIETY

'Gedi One Ter'

BACKGROUND OF THE INVENTION

Figure 1:
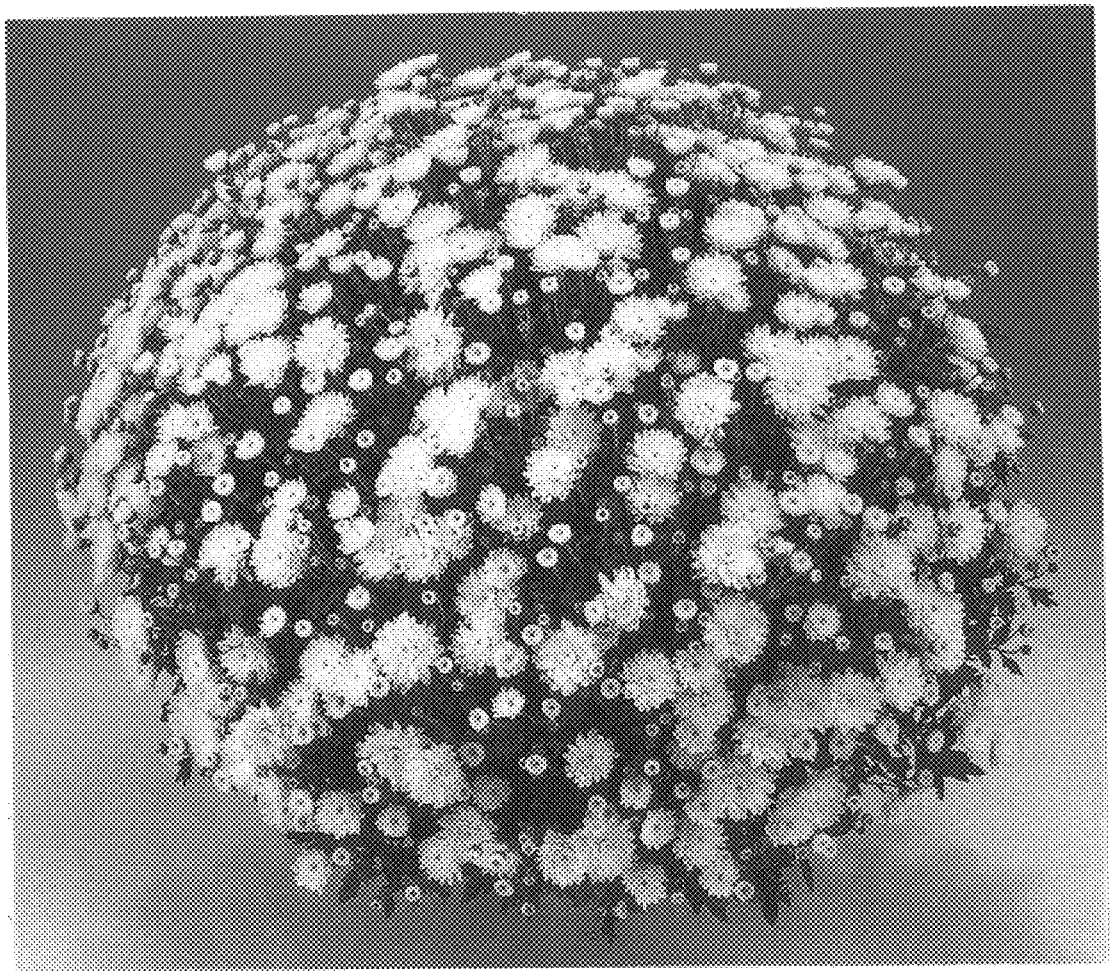

The present invention relates to a new and distinct cultivar of Chrysanthemum plant, botanically known as *Dendranthema morifolium* and herein after referred to by the cultivar name 'Gedi One Ter.'

The new cultivar is a product of hybridization of a female parent Chrysanthemum cultivar (unpatented, undistributed, unnamed seedling) and a male parent 'Subito,' (unpatented.) The new cultivar was discovered and selected by the inventor in October 1997.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'Gedi One Ter' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi One Ter'. These observations were made on plants approximately 135 days old from rooted cuttings. These characteristics in combination distinguish 'Gedi One Ter' as a new and distinct Chrysanthemum cultivar:

1. Large decorative type inflorescence;

2. Consistent flowering response to short days, blooming consistently after 49 days of short day length;

3. Free branching habit; and

4. Consistent natural season flowering habit during the last two weeks of August.

Plants of the new cultivar are similar to plants of the female and male parent cultivars in most horticultural characteristics, however plants of the new cultivar differed from plants of the parent cultivars in several characteristics. In comparison the new cultivar differed from the parents in the following characteristics:

1. The new cultivar has a wider diameter flower than the female parent;

2. The new cultivar has many more ray florets than the female parent;

3. The new cultivar naturally blooms three weeks earlier than the female parent;

4. The new cultivar has a wider diameter flower than the male parent;

5. The new cultivar has many more ray florets than the male parent; and

6. The new cultivar has different color ray florets than the male parent.

BRIEF DESCRIPTION OF THE PHOTOGRAPHS

The photograph shows a plant of the new cultivar which was grown in a 2-gallon container. A single cutting was grown in the container, and the plant was grown in outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000. The growing conditions range from 60° to 65° F. at night to 70° to 85° F. during the day. Measurements and numerical values represent averages of typical flowering types.

Botanical classification: *Dendranthema morifolium* cultivar 'Gedi One Ter'.

Commercial classification: Garden-type Chrysanthemum.
Parentage: Hybridization of female parent Chrysanthemum plant (unpatented) and male parent Chrysanthemum cultivar 'Subito'.

PROPAGATION

Time to rooting: 7 to 14 days at approximately 21° C.
Root description: Fine, fibrous.

PLANT

Growth habit: Mounding herbaceous perennial.
Height: Approximately 25 cm.
Plant spread: Approximately 28 cm.
Growth rate: Moderate.
Branching characteristics: Free branching.
Internode length: Approximately 2.5 cm.

FOLIAGE

Leaf:
*Arrangement.*—Alternate, single.
*Average length.*—Approximately 7.8 cm.
*Average width.*—Approximately 4 cm.
*Shape of blade.*—Ovate.
*Apex.*—Acuminate.
*Base.*—Attenuate.
*Attachment.*—Stalked.
*Margin.*—Pinnately lobed and teethed.
*Texture of top surface.*—Lightly pubescent.
*Texture of bottom surface.*—Lightly pubescent.
*Color.*—Young foliage upper side: Near 137B. Young foliage under side: Near 137B. Mature foliage upper side: Near 137A. Mature foliage under side: Near 137A. Venation upper side: Near 138C. Venation under side: Near 138C.

Petiole:
*Average length.*—Approximately 2.5 cm.
*Color:*—Near 137B.
*Diameter.*—Approximately 0.3 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the last two weeks in August.
*Number of inflorescences per stem.*—Approximately 13.
*Inflorescence diameter.*—Approximately 7 cm.
*Inflorescence depth.*—2.0 cm.
*Inflorescence longevity on plant.*—Approximately 26–29 days.
*Persistence.*—Persistent.

Ray florets:
*Appearance.*—Matte.
*Texture.*—Smooth.
*Average number per flower.*—300.
*Shape.*—Oblanceolate.
*Margin.*—Entire.
*Apex.*—Obtuse.
*Length.*—Approximately 4 cm.
*Width.*—Approximately 1 cm.
*Color.*—Upper surface at first opening: Near 158B. Upper surface at maturity: Near 155D. Upper surface at fading: Near 155D. Under surface at first opening: Near 158C. Under surface at maturity: Near 155D. Under surface at fading: Near 155D. Center ray florets color: Near 4D at maturity and fading.

Disc florets:
*Appearance.*—Shiny.
*Texture.*—Smooth.
*Average number per flower.*—Approximately 40.
*Shape.*—Cylindric.
*Apex.*—Obtuse.
*Average length.*—Approximately 1 cm.
*Average width.*—Approximately 0.2 cm.
*Color.*—At first opening: Near 8C. At maturity: Near 12B. At fading: Near 15C.

Peduncle:
*Length.*—At terminal end (shortest): Approximately 7 cm. At lateral end (longest): Approximately 12 cm.
*Diameter.*—Approximately 0.4 cm.
*Strength.*—Moderate.
*Color.*—Near 137C.
*Habit.*—Erect.
*Surface testure.*—Lightly pubescent.

Inflorescence bud:
*Length.*—Approximately 1 cm.
*Diameter.*—Approximately 1 cm.
*Form.*—Globular.
*Color.*—Near 8D.

Phyllaries:
*Appearance.*—Matte.
*Texture.*—Lightly pubescent.
*Number.*—Approximately 40 to 50.
*Shape.*—Ovate.
*Margin.*—Entire.
*Apex.*—Acute.
*Diameter.*—Approximately 0.3 cm.
*Length.*—Approximately 0.4 cm.
*Color.*—Upper side: Near 137A. Under side: Near 137A.

REPRODUCTIVE ORGANS

Ray florets:
*Number of pistils per flower.*—1.
*Stigma shape.*—2 branched.
*Stigma color.*—Near 16D.
*Style color.*—Near 16D.
*Style length.*—0.6 cm.
*Stamens.*—Absent.

Disc florets:
*Number of pistils per flower.*—1.
*Stigma shape.*—Cylindric.
*Style length.*—0.5 cm.
*Number of stamens per flower.*—Approximately 5.
*Anther shape.*—Tubular.
*Anther color.*—Near 16A.
*Pollen color.*—Near 17B.

OTHER CHARACTERISTICS

Seed production: Commercially, this plant is not used or observed in a stage wherein seeds would be produced. Therefore, seed production has not been observed.
Flower fragrance: Absent.

What is claimed is:

1. A new and distinct cultivar of Chrysanthemum plant named 'Gedi One Ter' as herein illustrated and described.

* * * * *